United States Patent [19]

Adams et al.

[11] 4,434,234

[45] Feb. 28, 1984

[54] METHOD AND KIT FOR SILVER STAINING SUBSTANCES SUPPORTED IN MATRIX

[75] Inventors: Lonnie D. Adams, Gobles; David W. Sammons, Kalamazoo, both of Mich.

[73] Assignee: The Upjohn Company, Kalamazoo, Mich.

[21] Appl. No.: 386,505

[22] Filed: Jun. 9, 1982

Related U.S. Application Data

[63] Continuation-in-part of Ser. No. 250,512, Apr. 2, 1981, abandoned.

[51] Int. Cl.$^3$ ............................................. G01N 33/68
[52] U.S. Cl. ....................................... 436/86; 422/61; 436/63; 436/174
[58] Field of Search ................ 424/3; 422/61; 436/86, 436/63, 174

[56] References Cited

U.S. PATENT DOCUMENTS 4,239,495  12/1980  Gindler .................................. 424/3

OTHER PUBLICATIONS

C. R. Merril et al., Anal. Biochem., 110(1), 201–207 (1981).
D. Goldman et al. Clin. Chem., 26(9), 1317–1322 (1980).

*Primary Examiner*—Sidney Marantz
*Attorney, Agent, or Firm*—L. Ruth Hattan

[57] ABSTRACT

A silver stain procedure wherein a substance capable of binding silver is treated with an aqueous silver salt solution, a reducing solution and an aqueous carbonate or sulfate salt solution and kit useful in practicing same.

15 Claims, No Drawings

METHOD AND KIT FOR SILVER STAINING SUBSTANCES SUPPORTED IN MATRIX

CROSS REFERENCE TO RELATED APPLICATION

This application is a continuation-in-part of copending application Ser. No. 250,512, filed Apr. 2, 1981, now abandoned.

FIELD OF INVENTION

The present invention involves a novel silver staining method and a kit useful in practicing said method.

BACKGROUND OF INVENTION

There are a number of known methods useful in staining proteins which utilize silver. For example, L. Kerenyi, et al., Clin. Chim. Acta 38, 465–467 (1972) describes a method for demonstrating proteins in electrophoretic, immunoelectrophoretic and immunodiffusion preparations whereby the preparations are treated with potassium ferrocyanide which is transformed during development into silver ferrocyanide then into colloidal silver grains. The physical developer contains anhydrous sodium carbonate, ammonium nitrate, silver nitrate, tungstosilicic acid and formalin, and the protein in the preparations stain dark brown with a pale gray background.

R. C. Switzer, et al., Anal. Biochem. 98, 231–237 (1979) and C. R. Merril, et al., Proc. Nat'l. Acad. Sci. U.S.A., 76, No. 9, 4335–4339 (1979) describe a silver stain technique for detecting proteins and peptides in polyacrylamide gel which is a modification of de Olmos' neural, cupric-silver stain. The procedure consists of ten steps and utilizes an aqueous solution of silver nitrate and cupric nitrate and involves treatment with a diammine solution which is known to sometimes form an explosive silver amide complex. The proteins stain as dark spots on a darkened background.

B. A. Oakley, et al., Anal. Biochem. 105, 361–363 (1980) simplified the above procedure of Switzer, et al., by reducing the number of steps involved to six and also reducing the amount of silver required without diminishing the sensitivity of the technique. However, the manner in which the proteins stain was not changed, i.e., dark stain on a darkened background.

A further modification of the Switzer, et al., procedure was made by R. C. Allen, Electrophoresis I, 32–37 (1980) who increased the sodium to ammonium ion ratio which resulted in increased silver deposition.

C. R. Merrill, et al., Anal. Biochem. 110, 201–207 (1981) modified and simplified the above procedure of Kerenyi, et al., adapting it to acrylamide gels.

D. Goldman, et al., Clin. Chem. 26, No. 9, 1317–1322 (1980) report that when using a procedure essentially the same as that of Merrill, et al., (PNAS, 1976) and Switzer, et al., (Anal. Biochem., 1979) proteins from samples of cerebral spinal fluid stained in shades of yellow, red and blue.

C. R. Merrill, et al., Science 211, 1437–1438 (1981) describe a silver stain procedure for proteins separated by two dimensional gel electrophoresis which requires treatment with potassium dichromate and nitric acid prior to staining with silver nitrate followed by washing then immersion in an image developer containing formalin and sodium carbonate. There is no indication of color development with this stain procedure.

Poehling and Neuhoff, Electrophoresis 1981, 2, 141–147, describe a silver stain suitable for acrylamide gels of 0.5 to 1 mm thickness which requires a pretreatment with glutardialdehyde under controlled temperatures prior to staining with a diamine solution.

Marshall and Latner, Electrophoresis 1981, 2, 228–235, describe a silver stain method which requires a treatment with paraformaldehyde and sodium cacodylate prior to staining with a modified diamine solution wherein methylamine is substituted for ammonium hydroxide. We have described the basic staining procedure of the present invention in Electrophoresis 1981, 2 135–145 and said procedure was included in a comparative study of certain staining methods reported by Ochs, et al., Electrophoresis 1981, 2, 304–307.

With the exception of the 1980 Goldman, et al., procedure all of the silver stain techniques known heretofore only stain proteins in varying shades of brown or black.

The present invention provids a unique stain procedure which not only is highly sensitive, but also, enables one to stain a variety of substances including proteins in varying shades of color.

SUMMARY OF INVENTION

The present invention is a method for staining various types or classes of compounds which is highly sensitive enabling one to detect picogram quantities of compounds or substances, and also is unique in that the method imparts color of the various substances staining them in varying shades of blue, green, red, and yellow. The present method will stain any substance that is capable of binding silver.

The present invention provides a novel method for staining substances capable of binding silver and which are supported in or on a matrix which comprises the steps of equilibrating said substance in a suitable silver salt solution, briefly rinsing said substance in water, then subjecting said substance to a reducing solution, and immersing said substance in a first, then a second and optionally a third sulfate or carbonate salt solution.

The substances to be stained bind silver according to their unique composition, thereby resulting in a characteristic color. The present method is particularly suited for staining proteins. The color adds a new dimension to the separation and identification of proteins, as well as other substances, by electrophoresis by aiding for example in the resolution of overlapping proteins and identifying members of a family of proteins by their characteristic color. Thus the method of the present invention which is both sensitive and reproducible will facilitate the identification of substances or compounds that are diagnostic markers and/or primary lesions of most genetic diseases including the major diseases such as diabetes, atherosclerosis and cancer. In addition, pathological changes in tissues can be correlated with changes in certain substances, particularly proteins. The present invention provides a means to enhance ones understanding of normal and disease conditions. Also, the present invention is particularly useful in detecting minute amounts of proteins separated from samples required for forensic medicine.

Another aspect of the present invention is a kit wherein the component parts are assembled in a manner to facilitate the practice of the silver staining method of the present invention, said kit comprising multiple containers having therein appropriate amounts of reagents necessary to practice said method as follows:

(a) a container having therein a suitable silver salt;

(b) a container having therein an appropriate base solution;

(c) a container having therein an aldehyde solution; and (d) a container having therein an appropriate amount of a carbonate or sulfate salt.

Generally the quantity of silver salt contained in the kit for 10 gels (8 cm×7 cm×1.5 mm) will be up to 6.0 grams and preferably will be 1.85 to 2.0 grams; the quantity of base will vary from 100 to 150 ml; the quantity of aldehyde will vary from about 12 to 20 ml; and the amount of carbonate or sulfate salt will vary from about 20 to 70 grams.

DETAILED DESCRIPTION OF INVENTION

The method of the present invention is useful to stain any substance or compound which is capable of binding silver. Such substances include proteins, polypeptides, amino acids, nucleic acids and polymers thereof, lipids, carbohydrates including starches and sugars of various classes, e.g., oligosaccharides, or polysaccharides, such as mucoitin sulfate, lipoproteins, glucoproteins, nucleoproteins, including ribonucleic- and deoxyribonucleic-protein complexes, mucopolysaccharides, e.g., chondroitin, proteoglycans, mucolipids, such as ganglioside, mucoproteins, and glycolipids. We have found that the present method is particularly useful in identifying families of proteins, i.e., proteins comprised of the same protein subunits but which may be conjugated to other chemical entities, such as, a saccharide thereby altering the overall net charge or character of the protein.

It is important when staining the sample of substance supported in a matrix, such substance so supported being referred to hereinafter as "matrix preparation," by the method of the present invention that said matrix preparation be washed thoroughly to remove any components which may interfere with the uptake of silver by the substance to be stained. The matrix preparation should be washed repeatedly, for example, in a lower alkanol, such as methanol or ethanol containing a mild acid, such as, trichloroacetic acid or acetic acid. We have found that methanol diminishes the color range of the visible spectra somewhat whereas ethanol does not. Also when trichloroacetic acid is used it is very important that the matrix preparation be washed subsequently very thoroughly with water or ethanol-water mixture. Generally, for a 1.5 mm thick gel, washing for 2 to 12 hours is adequate using for each milliliter (ml) of matrix 5.5 ml of solution, and for a 0.1 mm thick gel, washing one to 3 hours with several changes of solution using for each ml of matrix 15 ml of solution per change. Of course, less time is required for thinner gels. Various washing regimens may be employed. Those found to be most suitable and/or expeditious are described in detail hereinbelow in the "General Procedure." This washing procedure is commonly referred to as fixation/washing.

The present novel staining method can be used to stain virtually any substance which is capable of binding silver and typically is useful in staining such substances which have been separated using one or two dimensional electrophoresis techniques. The matrix in which the substance to be stained is supported can be comprised of any materials which are commonly used in electrophoretic procedures. For example, the matrix may consist of derivatized paper that is useful for electrophoretic protein transfer, cellulose acetate, starch gel, agarose, Sephadex beads, or polyacrylamide, and may vary in thickness from an ultrathin matrix of about 50 microns to 3 mm. For thicker gels, e.g., 1.5–3.0 mm carbohydrate containing matrices are less preferred due to dark background staining. It may be desirable to attach the matrix on a nylon mesh, a glass plate, or a plastic sheet for additional support. As is known from standard electrophoretic techniques, the density and pore size of the matrix may also vary. A preferred matrix composition is polyacrylamide, varying from 50 microns to 3.0 mm in thickness with 1.5 mm being the most preferred thickness.

We have found that the present method is especially useful for staining substances, and, in particular, proteins that have been separated by two dimensional electrophoresis on polyacrylamide gels. The method of the present invention is particularly useful for staining substances separated using the ISO-DALT system of Anderson and Anderson, Anal. Biochem. 85, 331–340 and 341–354 (1978). When staining substances separated by the ISO-DALT system, sequential washing with agitation of the gel preparation for example in solutions of ethanol or methanol of concentrations varying from about 50% to 40% to 25% to 10% containing a suitable mild acid, such as acetic acid, at a concentration of 10% in the first three solutions and 0.5% in the final solution, is generally adequate to remove any sodium dodecyl sulfate contained in the gel. The method of the present invention is also useful for staining substances separated on ultrathin gels prepared by the method of Gorg, et al., Anal. Biochem., 1979, 89, 60–70, and Radola, Electrophoresis, 1980, 1, 43–56.

With the method of the present invention we have been able to detect picogram quantities of substances and obtain matrix preparations which stain in varying shades of blue, green, yellow and red. The background of the matrix preparation stains in light shades of yellow to orange upon which the brightly colored substances are detected easily. The intensity of the color will vary somewhat with the thickness of the matrix as well as with the concentration of the substance to be stained. For best results a matrix of 1.5 mm thickness of 10% to 20% polyacrylamide gel is used.

The novel silver stain procedure described and claimed herein is highly sensitive, gives high resolution of substances, is reproducible, is easy to use, and is efficient in that matrix preparations can be stained batch-wise. Additionally the entire procedure is carried out at room temperature, i.e., about 18° to 27° C. with standard room lighting, there being no requirement of elevated temperatures or special light control.

Suitable silver salts which may be used in the present invention are those which will dissociate in water to give free silver ion and which will not complex with the reducing agents employed in the method. Aqueous solutions of silver nitrate or silver acetate are particularly suitable for use in the present invention. The silver salt is dissolved in water, generally distilled water, at a concentration of from about 0.5 to 6 grams of silver salt per liter of water. The lower concentration of silver salt, i.e., 1 gram/liter results in reduced sensitivity and intensity and the background of the matrix stains lighter than at the higher concentrations of silver salt. When ultrathion matrices are used concentrations of silver salt varying from about 3 to 6 grams of salt per liter of water are preferred, and the matrix preparation is equilibrated in the silver salt solution for about 10 minutes to 2 hours using for each 1 ml of matrix about 15 ml of solution. A preferred concentration of silver salt for thicker gels, i.e., 0.75 to 1.5 mm, is about 1.5 to 2.0 grams/liter, and the more preferred concentration is about 1.90 grams/liter. The 1.5 mm thick matrix preparation is equilibrated in the silver salt solution for about 30 minutes to 2 hours using for each 1 ml of matrix about 3 ml of solution. Of course as thicker matrix preparations are employed time required to equilibrate is longer.

Following equilibration in the silver salt solution the matrix preparation is washed briefly in water to remove any surface silver, then the preparation is subjected to a reducing solution. The reducing solution may be sprayed onto the matrix preparation, particularly when thin matrix preparations are being stained, or the matrix preparation may be immersed in the reducing solution. The reducing solution consists of a base such as aqueous potassium hydroxide or sodium hydroxide or sodium or potassium carbonate and an aldehyde, such as, formaldehyde, acetaldehyde, n-butyraldehyde, or glutaraldehyde. The concentration of base may vary from about 0.5 to 1.0 N with 0.75 N base, preferably sodium hydroxide, being the most suitable. The preferred reducing agent is formaldehyde and generally a 37% solution is employed. Generally for gels which are 1.0 mm or thicker the reducing solution will comprise about 1 to 5 ml of 37% formalin per about each 400 ml of aqueous base. A preferred reducing solution consists of per each 390 ml of 0.75 N NaOH, and 3 ml of 37% formalin. For each ml of matrix preparation one should use about 5.5 ml of reducing solution. Generally for gels thinner than 1 mm the reducing solution will comprise about 0.75 to 1.5 ml of 37% formalin per about each 150 ml of aqueous base. A preferred reducing solution consists of per each 150 ml of 0.75 N NaOH, 1.1 ml of 37% formalin. For each ml of matrix preparation one should use about 15 ml of reducing solution. It is recommended that in preparing the reducing solution as well as other aqueous solutions described herein one use distilled deionized and degassed water. The reduction generally requires about 30 seconds to 15 minutes, and when the matrix preparation is submersed in the reducing solution agitation at about 40 cycles per minute is recommended. The time required for reduction varies with the thickness of the gels with time required increasing as the matrix thickness increases. We have found that for gels of about 1.0 to 3.0 mm in thickness about 5 to 15 minutes is adequate for reduction and for gels less than 1.0 mm in thickness about 30 seconds to 5 minutes is adequate. The reaction time could be shortened if the temperature is raised.

When sodium carbonate as a 3% solution is used as the base in the reducing solution the background matrix has a tendency to stain very dark which may obscure the color staining pattern. The dark background can be overcome in several ways. For example, the length of time the matrix preparation is subjected to the reducing solution may be shortened followed by treatment with a mild acid, such as acetic acid. Also, by placing the matrix preparation in the sodium carbonate solution then carefully titrating the aldehyde, preferably a formaldehyde, the dark background staining is avoided. Also, by careful addition of an oxidizing agent such as sodium sulfite to prevent rapid and extensive surface reaction the dark background staining is prevented. Although sodium carbonate is useful as a base in the reducing solution, it is not preferred in view of the additional preparative steps required to give a satisfactory product.

Generally the components of the reducing solution are mixed together and the matrix preparation previously equilibrated in the silver salt solution is brought into contact with the resultant solution. The reduction step may also be achieved by first contacting the matrix preparation with a suitable base solution followed by the addition of the aldehyde, however, the reverse addition of components is less desirable.

Following reduction the matrix preparation is immersed for about one hour for gels of about 1.0 to 3.0 mm thickness and for about 1 to 15 minutes for gels less than 1.0 mm thickness in an 0.075 to 1.5 percent (%) anhydrous sodium or potassium carbonate solution or a sodium or potassium sulfate solution having a pH of 11 or greater followed by immersion in a second sodium or potassium carbonate or sulfate solution which may vary in concentration from about 0.15 to 3.0%, preferably about 0.75%. We have found that the use of two carbonate or sulfate solutions is generally adequate, however, immersion of the gel preparation in a third carbonate or sulfate solution preferably of about 0.75% concentration will have only a beneficial effect insofar as color development and maintenance of said color is concerned. For the thicker gels, i.e., 1.0 to 3.0 mm, the matrix preparation may be stored in the second or third carbonate or sulfate salt solution which also has a pH of 11 or greater. For thinner gels of up to 1.0 mm thickness the matrix preparation should be rinsed with water following the second or third treatment with carbonate or sulfate solution and then air dried. Sodium carbonate is preferred for this step. For the thicker gels optimal color develops in about 6 hours. Color development results in varying shades of black and brown, blue, green, yellow, and red. The stained preparation may be photographed by standard well known techniques. If one wishes, for example, in those instances where color photography is not practicable, the color development may be avoided by substituting ammonium carbonate or ammonium sulfate for sodium carbonate or sulfate in the final wash solutions. The quantity of ammonium carbonate or ammonium sulfate employed may vary from 1% to 3% with 1.5% being particularly suitable. The resultant matrix preparation will be stained in varying shades of brown, black and yellow.

As indicated hereinabove standard electrophoretic procedures may be used to separate the substances to be stained in either one dimension or two dimensions. When such substances have been separated using standard two dimensional electrophoresis on polyacrylamide gel, it is very important to remove the SDS during the fixation/washing step. Also it is recommended that reagents of high quality be used. Additionally, it is recommended that for best results a freshly prepared solution of 2-mercaptoethanol, not to exceed 2%, be made up for reducing agent, and that sodium hydroxide and phosphoric acid be used for cathodic and anodic solutions respectively.

When preparing the sample of substance to be stained the concentration for each sample will have to be adjusted individually. Generally, we find that samples should be diluted 10 to 50 times of those used for staining by conventional Coomassie Blue procedures.

As used herein thinner gels means gels of about 50 microns to 1.0 mm and thicker gels means gels of about 1.0 to 3.0 mm thickness.

A preferred general procedure is the following.

GENERAL PROCEDURE

Tissue samples or samples of substances to be stained are prepared and run on first and second dimension gels according to the procedure described by Anderson and Anderson, ibid. Second dimension gels are fixed in 50% ethanol/10% acetic acid for two or more hours with one change of fixative. The gels are then washed two times in 25% ethanol/10% acetic acid and two times in 10% ethanol/0.5% acetic acid (one hour each) to remove any remaining sodium dodecyl sulfate (SDS). Or, following fixation in 50% ethanol/10% acetic acid the gels are washed two times in 25% ethanol/10% acetic acid for two hours each followed by either four one-hour water washes or six 30-minute water washes, the latter of which is preferred. Next the gels are soaked for at least 30 minutes in 1.9 g/l $AgNO_3$ in water for thicker gels and for at least 10 minutes in 4 g/l $AgNO_3$ in water for thinner gels. Gels are removed from the silver solution and processed singly or in groups of up to five or more. Single gels of 1.0 to 3.0 mm thickness are rinsed in deionized water and then placed in a rectangular glass dish 28×18×4 cm. To this dish is added reducing solution which consists of 390 ml 0.75 N NaOH, 3 ml of 37% formaldehyde. The dish is placed on a shaker for 10 minutes, then the reducing solution is poured off and replaced with an equal volume of 0.75% $Na_2CO_3$. After an hour the $Na_2CO_3$ solution is replaced with fresh 0.75% $Na_2CO_3$ solution and optionally a third such solution and the gel is stored in the last solution used.

Single gels of 50 microns to 1.0 mm thickness are then placed in a rectangular glass dish 10×10×1 cm. To this dish is added reducing solution which consists of 15 ml 0.75 N NaOH and 0.1 ml of 37% formaldehyde. The dish is placed on a shaker for 30 seconds, then the reducing solution is poured off and replaced with an equal volume of 0.75% $Na_2CO_3$. The sodium carbonate solution is changed two or three times at one- to 15-minute intervals.

For more than one gel, appropriately larger volumes of reducing solution and $Na_2CO_3$ solution are used. Also, it may be useful to cover the glass dishes with, e.g., a plastic wrap to help avoid evaporation of the solutions.

EXAMPLE 1

In order to determine the sensitivity of the staining method and to determine the effect, if any, of concentration of protein on color, development mixtures of proteins of known concentrations were electrophoresed using the general procedure of the two dimensional ISO-DALT technique then stained by the General Procedure set forth above for thicker gels. Seven mixtures consisting of creatine kinase, myokinase, α-amylase, lactate dehydrogenase I (LDH-I) and glutamate-pyruvate transaminase (GPT) are prepared. The concentration of each of the proteins in any one mixture is the same, and the concentrations are 1 ng, 2 ng, 10 ng, 50 ng, 200 ng, 1 μg or 5 μg.

All five proteins can be seen clearly at the 5 μg, 1 μg and 200 ng concentrations, however, α-amylase and GPT are faint at the 200 ng concentration indicating that the sensitivity of the staining procedure varies somewhat with the protein. LDH-I can also be seen at the 50 ng, 10 ng and 2 ng concentrations. No protein at the 1 ng concentration is detected. At the 2 ng level LDH-I appears as 3 spots very close together which indicates each spot represents less than 1 ng of protein.

The proteins stained the following colors: Creatine kinase, blue-green; myokinase, yellow; alpha amylase, a red shade; LDH-I, blue-gray; and GPT, blue-gray. At low concentrations the hue of the proteins was unchanged as a function of concentration. However, at higher saturated concentrations of protein mixed colors result. For example, at concentrations of 5 μg and 1 μg LDH-I spots have a red center with a blue margin. Also, at a concentration of 5 μg the myokinase spot has a black center with a yellow margin. The mixed color is believed to be due to an absence of uniform silver deposition throughout the protein spot.

EXAMPLE 2

The significant reagents for the performance of the staining procedure are assembled into a mercantile kit, specifically, a kit for marketing to qualified individuals to perform the staining procedure. The kit comprises as basic components at least four containers, one of each having therein appropriate amounts of a suitable silver salt; a suitable base; a suitable aldehyde reducing agent; or an appropriate amount of sodium carbonate.

A preferred kit composition is one designed to stain 6 gels which are 1.5 mm thick and are 18 cm×20 cm wherein one container has therein 1.85 to 2.0 grams of silver nitrate; another container has therein 120 ml of 50% sodium hydroxide; another container has therein 16 ml of 37% formalin; and two additional containers have therein 22 grams of sodium carbonate.

We claim:

1. A method for silver staining a substance supported in a matrix, comprising:
    (a) equilibrating said substance in an aqueous silver salt solution;
    (b) rinsing said substance in water;
    (c) subjecting said substance to a reducing solution; and
    (d) immersing said substance in a first, then a second aqueous carbonate or aqueous sulfate salt solution.

2. The method of claim 1 wherein said substance is protein, a polypeptide or a protein containing substance.

3. The method of claims 1 or 2 further comprising: fixing and washing said substance in an aqueous lower alkanol solution containing a mild acid prior to equilibrating step (a).

4. The method of claim 3 wherein the lower alkanol is ethanol.

5. The method of claim 4 wherein the mild acid is acetic acid.

6. The method of claims 1 or 2 wherein the matrix is polyacrylamide gel.

7. The method of claims 1 or 2 wherein the silver salt is silver nitrate.

8. The method of claims 1 or 2 wherein the reducing solution comprises formaldehyde and a base selected from the group consisting of aqueous potassium hydroxide and aqueous sodium hydroxide.

9. The method of claims 1 or 2 wherein equilibrating step (a) extends from about 30 minutes to 2 hours, reducing step (c) extends from about 5 to 15 minutes and wherein the first and second immersions of step (d) are about one hour and about six hours, respectively.

10. The method of claim 9 wherein step (d) further includes a third immersion in an aqueous carbonate or aqueous sulfate salt solution.

11. The method of claims 1 or 2 wherein equilibrating step (a) extends from about 10 minutes to two hours, reducing step (c) extends from about 30 seconds to five minutes and wherein the first and second immersions of step (d) are each about one to 15 minutes.

12. A method for silver staining a protein, polypeptide or protein containing substance which is supported in a matrix which comprising equilibrating said substance for about two hours in an aqueous silver nitrate solution containing from about 0.5 to 6 grams of silver salt per liter of water, briefly washing said substance in water, then subjecting said substance for about 5 to 15 minutes to a reducing solution comprising about 1 to 5 ml of 37% formalin followed by immersing said substance in a first 0.075 to 1.5% aqueous sodium carbonate solution for about one hour, then a second 0.15 to 3% aqueous carbonate solution for a total of about six hours.

13. The method of claim 12 wherein step (d) further includes a third immersion in a 0.15 to 3% aqueous sodium carbonate solution.

14. A mercantile kit comprising multiple containers wherein is contained separately the following reagents: a silver salt, a base solution, an aldehyde solution and a carbonate or sulfate salt.

15. The kit of claim 14 wherein one container has therein 1.85 to 2.0 grams of silver nitrate; a second container has therein 120 ml of 50% sodium hydroxide; a third container has therein 16 ml of 37% formalin; and two additional containers each has therein 22 grams of sodium carbonate.

* * * * *